United States Patent [19]

Frangi et al.

[11] Patent Number: 5,484,594
[45] Date of Patent: Jan. 16, 1996

[54] PROCESS FOR PREPARING GRAPESEED EXTRACTS ENRICHED IN PROCYANIDOL OLIGOMERS

[75] Inventors: Enrico Frangi; Marco Bertani; Giuseppe Mustich; Gianfranco Tuccini, all of Milan, Italy

[73] Assignees: Tecnofarmaci S.p.A., Pomezia; Indena S.p.A., Milan, both of Italy

[21] Appl. No.: 949,733

[22] Filed: Sep. 23, 1992

Related U.S. Application Data

[63] Continuation-in-part of Ser. No. 371,591, Jun. 26, 1989, abandoned.

[30] Foreign Application Priority Data

Jun. 28, 1988 [IT] Italy ........................... 21134/88

[51] Int. Cl.⁶ ................................................. A61K 35/78
[52] U.S. Cl. ........................................ 424/195.1; 210/650
[58] Field of Search ........................... 424/195.1; 210/650

[56] References Cited

U.S. PATENT DOCUMENTS 4,698,360 10/1987 Masquelier ........................ 514/456
4,963,527 10/1990 Bombardelli ........................ 514/25

FOREIGN PATENT DOCUMENTS 0348781 1/1990 European Pat. Off. ............ 424/195.1
1541469 2/1979 United Kingdom ................ 424/195.1

OTHER PUBLICATIONS

McGregor, W. C., Membrane Separations in Biotech Marcel Dekker, N.Y., 1986, pp. 61–64, 161, 201–215.

Steinmetz, E. F., Codex Vegetabilis, Amsterdam, 1957, #1206.

*Primary Examiner*—Michael G. Wityshyn
*Assistant Examiner*—Ralph Gitomer
*Attorney, Agent, or Firm*—Bucknam and Archer

[57] ABSTRACT

An extract enriched in procyanidol oligomers almost free from monomers is obtained by subjecting a crude vegetable extract, for instance from *Vitis vinifera*, to ultrafiltration on membranes of cut-off from 3,000 to 600, or to a selective extraction with ethers, or esters or mixtures of ethyl acetate and aromatic hydrocarbons.

8 Claims, 8 Drawing Sheets

Report   File mus1.DT3

278 nm

| No. | Retention time | Height [AU] | Left time | Right time | Area [AU×min] | Area [%] | Mark |
|---|---|---|---|---|---|---|---|
| 1 | 4.35 | 0.0328 | 4.11 | 4.68 | 0.0007429 | 1.214 | H |
| 2 | 4.95 | 0.0055 | 4.61 | 5.28 | 0.0001487 | 0.243 | H |
| 3 | 5.49 | 0.0273 | 5.22 | 6.09 | 0.0097710 | 1.587 | V |
| 4 | 6.62 | 0.1752 | 6.09 | 7.76 | 0.0574455 | 9.388 | H |
| 5 | 8.03 | 0.0019 | 7.76 | 8.77 | 0.0006623 | 0.102 | H |
| 6 | 11.41 | 0.0026 | 10.07 | 12.21 | 0.0016607 | 0.263 | H |
| 7 | 13.14 | 0.0384 | 12.51 | 14.08 | 0.0187708 | 3.057 | H |
| 8 | 14.78 | 0.0039 | 14.08 | 15.38 | 0.0025940 | 0.424 | H |
| 9 | 16.02 | 0.0149 | 15.38 | 16.82 | 0.0092111 | 1.505 | H |
| 10 | 17.12 | 0.0024 | 16.82 | 18.39 | 0.0004180 | 0.068 | H |
| 11 | 17.99 | 0.1792 | 18.39 | 20.80 | 0.0835910 | 13.659 | H |
| 12 | 18.97 | 0.0126 | 20.80 | 22.97 | 0.0130630 | 2.135 | H |
| 13 | 21.74 | 0.0710 | 22.97 | 25.07 | 0.0339970 | 5.555 | H |
| 14 | 23.51 | 0.0016 | 25.04 | 26.04 | 0.0004342 | 0.071 | H |
| 15 | 25.98 | 0.1925 | 26.04 | 27.45 | 0.0006623 | 0.102 | H |
| 16 | 26.18 | 0.1111 | 27.45 | 29.25 | 0.0821960 | 13.431 | H |
| 17 | 28.75 | 0.0143 | 29.25 | 30.02 | 0.0050440 | 0.824 | H |
| 18 | 29.35 | 0.0070 | 30.02 | 31.29 | 0.0071380 | 1.166 | H |
| 19 | 31.86 | 0.0211 | 31.29 | 32.46 | 0.0038700 | 0.632 | H |
| 20 | 32.93 | 0.0321 | 32.46 | 34.53 | 0.0173180 | 2.830 | V |
| 21 | 34.50 | 0.0051 | 34.53 | 34.67 | 0.0017260 | 0.282 | H |
| 22 | 35.20 | 0.0730 | 34.67 | 35.07 | 0.0374690 | 6.123 | H |
| 23 | 36.34 | 0.0025 | 35.07 | 37.81 | 0.0007430 | 0.121 | H |
| 24 | 37.06 | 0.0034 | 37.07 | 37.81 | 0.0032120 | 0.525 | H |
| 25 | 43.90 | 0.0036 | 41.89 | 44.19 | 0.0013380 | 0.219 | H |
| 26 | 44.67 | 0.0119 | 44.23 | 45.23 | 0.0060230 | 0.982 | H |
| 27 | 45.87 | 0.0270 | 45.23 | 47.14 | 0.0061110 | 0.999 | V |
| 28 | 47.91 | 0.0035 | 47.17 | 48.61 | 0.0010680 | 0.175 | H |
| 29 | 48.91 | 0.0133 | 47.61 | 49.24 | 0.0122320 | 0.417 | H |
| 30 | 50.68 | 0.0016 | 49.98 | 52.02 | 0.0086730 | 1.093 | H |
| 31 | 54.06 | 0.0037 | 53.72 | 54.59 | 0.0005660 | 0.093 | H |
| 32 | 56.83 | 0.0022 | 55.93 | 57.30 | 0.0015720 | 0.257 | H |
| 33 | 57.77 | 0.0015 | 57.30 | 58.10 | 0.0007650 | 0.125 | H |
| 34 | 58.77 | 0.0016 | 58.47 | 59.34 | 0.0006350 | 0.104 | TB |
| 35 | 60.37 | 0.0284 | 58.10 | 60.68 | 0.0287750 | 4.702 | V |
| 36 | 61.41 | 0.0375 | 60.68 | 61.54 | 0.0213930 | 3.496 | V |
| 37 | 62.38 | 0.0033 | 61.54 | 65.12 | 0.1215560 | 19.863 | TA |
| 38 | 63.68 | 0.0015 | 63.08 | 65.12 | 0.0033140 | 0.541 | I |
| 39 | 72.15 | | 71.81 | 73.35 | 0.0005010 | 0.082 | |

Report File mus2.DT3

278 nm

| No. | Retention time | Height [AU] | Left time | Right time | Area [AU*min] | Area [%] | Mark |
|---|---|---|---|---|---|---|---|
| 1 | 4.36 | 0.0292 | 4.16 | 4.69 | 0.006541 | 1.512 | H |
| 2 | 4.96 | 0.0069 | 4.62 | 5.23 | 0.002321 | 0.537 | H |
| 3 | 5.50 | 0.0263 | 5.19 | 6.23 | 0.010629 | 2.458 | V |
| 4 | 6.67 | 0.0117 | 6.23 | 6.87 | 0.005683 | 1.314 | V |
| 5 | 7.07 | 0.0101 | 6.87 | 11.85 | 0.014991 | 3.466 | H |
| 6 | 13.42 | 0.0587 | 12.72 | 14.49 | 0.029967 | 6.929 | H |
| 7 | 15.16 | 0.0066 | 14.76 | 15.76 | 0.004324 | 1.000 | H |
| 8 | 16.39 | 0.0128 | 15.76 | 17.20 | 0.008100 | 1.873 | H |
| 9 | 17.50 | 0.0034 | 17.20 | 18.23 | 0.001299 | 0.300 | H |
| 10 | 19.54 | 0.0327 | 18.93 | 20.10 | 0.017689 | 4.090 | H |
| 11 | 20.47 | 0.0112 | 20.10 | 21.27 | 0.006968 | 1.611 | H |
| 12 | 22.48 | 0.0082 | 21.27 | 23.48 | 0.008517 | 1.969 | H |
| 13 | 24.25 | 0.0808 | 23.45 | 25.59 | 0.040267 | 9.310 | H |
| 14 | 26.09 | 0.0144 | 25.59 | 26.55 | 0.006398 | 1.479 | H |
| 15 | 26.76 | 0.0038 | 26.55 | 27.16 | 0.001080 | 0.250 | H |
| 16 | 27.52 | 0.0048 | 27.16 | 28.26 | 0.002256 | 0.522 | H |
| 17 | 28.73 | 0.0201 | 28.26 | 29.66 | 0.008218 | 1.900 | H |
| 18 | 30.30 | 0.0095 | 29.70 | 30.46 | 0.003829 | 0.885 | H |
| 19 | 30.80 | 0.0128 | 30.46 | 31.60 | 0.006507 | 1.504 | H |
| 20 | 32.31 | 0.0091 | 31.60 | 32.91 | 0.004988 | 1.153 | H |
| 21 | 33.31 | 0.0592 | 32.84 | 34.44 | 0.026183 | 6.054 | H |
| 22 | 36.58 | 0.0595 | 35.58 | 37.32 | 0.034112 | 7.887 | H |
| 23 | 37.62 | 0.0061 | 37.32 | 38.22 | 0.002138 | 0.494 | H |
| 24 | 39.32 | 0.0052 | 38.55 | 40.39 | 0.004776 | 1.104 | H |
| 25 | 39.96 | 0.0025 | 39.56 | 40.36 | 0.000988 | 0.228 | TA |
| 26 | 43.17 | 0.0053 | 42.06 | 44.17 | 0.004719 | 1.091 | H |
| 27 | 44.94 | 0.0041 | 44.24 | 45.41 | 0.002093 | 0.484 | H |
| 28 | 45.81 | 0.0046 | 45.41 | 46.41 | 0.002067 | 0.478 | H |
| 29 | 47.98 | 0.0016 | 47.65 | 48.58 | 0.000627 | 0.145 | H |
| 30 | 48.88 | 0.0020 | 48.58 | 49.82 | 0.001346 | 0.311 | H |
| 31 | 50.59 | 0.0125 | 49.95 | 51.79 | 0.007284 | 1.684 | H |
| 32 | 52.90 | 0.0020 | 52.50 | 53.56 | 0.000972 | 0.225 | H |
| 33 | 61.29 | 0.0297 | 57.81 | 69.31 | 0.136053 | 31.457 | TA |
| 34 | 62.99 | 0.0075 | 61.52 | 65.94 | 0.018573 | 4.294 | TA |

Report    File bis3.DT3

273 nm

| No. | Retention time | Height [AU] | Left time | Right time | Area [AU×min] | Area [%] | Mark |
|---|---|---|---|---|---|---|---|
| 1 | 4.31 | 0.0294 | 4.11 | 4.64 | 0.006615 | 1.417 | H |
| 2 | 4.91 | 0.0066 | 4.61 | 5.18 | 0.002045 | 0.438 | H |
| 3 | 5.41 | 0.0248 | 5.14 | 6.28 | 0.011106 | 2.379 | V |
| 4 | 6.65 | 0.0093 | 6.28 | 11.80 | 0.018461 | 3.954 | H |
| 5 | 13.44 | 0.0532 | 12.57 | 14.51 | 0.029186 | 6.251 | H |
| 6 | 15.28 | 0.0034 | 14.51 | 15.81 | 0.002539 | 0.544 | H |
| 7 | 16.41 | 0.0183 | 15.81 | 17.21 | 0.011372 | 2.436 | H |
| 8 | 19.52 | 0.0326 | 18.89 | 19.95 | 0.017963 | 3.847 | V |
| 9 | 20.26 | 0.0173 | 19.95 | 21.19 | 0.010863 | 2.327 | H |
| 10 | 22.36 | 0.0117 | 21.19 | 23.36 | 0.012593 | 2.697 | H |
| 11 | 24.23 | 0.0781 | 23.36 | 25.57 | 0.040098 | 8.588 | H |
| 12 | 26.00 | 0.0118 | 25.57 | 26.54 | 0.005318 | 1.139 | H |
| 13 | 28.78 | 0.0046 | 28.41 | 29.48 | 0.001904 | 0.408 | H |
| 14 | 30.15 | 0.0119 | 29.48 | 30.45 | 0.005362 | 1.148 | V |
| 15 | 30.75 | 0.0128 | 30.45 | 31.55 | 0.005791 | 1.240 | H |
| 16 | 32.22 | 0.0120 | 31.55 | 32.82 | 0.006340 | 1.358 | H |
| 17 | 33.26 | 0.0460 | 32.79 | 34.79 | 0.023761 | 5.089 | H |
| 18 | 36.57 | 0.0788 | 35.40 | 37.30 | 0.049296 | 10.558 | H |
| 19 | 38.74 | 0.0042 | 38.07 | 39.61 | 0.002791 | 0.598 | H |
| 20 | 42.98 | 0.0032 | 42.48 | 44.05 | 0.002630 | 0.563 | H |
| 21 | 44.92 | 0.0055 | 44.16 | 45.33 | 0.002821 | 0.604 | H |
| 22 | 45.76 | 0.0114 | 45.33 | 47.10 | 0.006133 | 1.314 | H |
| 23 | 48.07 | 0.0137 | 47.10 | 48.60 | 0.006690 | 1.433 | H |
| 24 | 48.94 | 0.0061 | 48.60 | 49.94 | 0.004102 | 0.879 | H |
| 25 | 50.61 | 0.0173 | 49.94 | 51.68 | 0.010355 | 2.218 | H |
| 26 | 52.88 | 0.0055 | 52.48 | 53.62 | 0.002432 | 0.521 | H |
| 27 | 60.13 | 0.0299 | 58.03 | 60.40 | 0.031098 | 6.661 | H |
| 28 | 61.10 | 0.0343 | 60.40 | 61.71 | 0.041744 | 8.941 | V |
| 29 | 62.04 | 0.0415 | 61.71 | 67.32 | 0.095486 | 20.451 | V |

FIG.5a

PROCESS FOR PREPARING GRAPESEED EXTRACTS ENRICHED IN PROCYANIDOL OLIGOMERS

This application is a continuation-in-part of U.S. Ser. No. 371,591 filed Jun. 26, 1989, now abandoned.

FIELD OF THE INVENTION

The present invention relates to novel procyanidol oligomeric fractions extracted from vegetables, to the processes for the preparation thereof and to pharmaceutical compositions containing them.

The extracts from *Vitis vinifera* grapeseeds, containing these oligomers, have already been used in therapy, particularly as vasoprotectors, in the treatment of disorders of the retinal or choroidal circulation and of venolymphatic insufficiencies; in fact, they increase the resistance of vessels and capillaries and decrease their permeability.

Procyanidol oligomers are polyphenols derived from flavanols, resulting from the oxidative condensations of various flavanolic units, which can be the same or different, particularly from the condensation of (+) catechin, epicatechin and gallocatechin. They are present in different vegetables, such as vine, apple-tree, maritime pine, hawthorn, cinchona, eucalyptus. They contain 2–7 catechin units.

BACKGROUND OF THE INVENTION

Extracts prepared according to the processes of the prior art, particularly the processes described in FR-A-2,092,743 and FR-A-2,372,823 concerning *Vitis vinifera*, the process described in FR 1,427,100 and in U.S. Pat. No. 4,698,360 concerning maritime pine, proved to contain, in addition to the oligomers of polymerization degree 2 to 7, condensation products of higher molecular weights (in spite of a treatment with a sodium chloride saturated aqueous solution) and, above all, monomers in the not negligible proportions of 20 to 30% by weight. These monomers are considered undesired substances. A medicinal proprietary product containing as the active ingredient only catechin, has been withdrawn from the market because of side effects.

Some side effects of flavonoids have been reported see Jaeger et al "Side Effects of Flavonoids in Medical Practice". Plant Flavonoids in Biology and Medicine II: Biochemical, Cellular, and Medicinal Properties, pages 379–394 (1988).

British patent 1,541,469 describes a process consisting of extracting the organic matter with an acetone-water mixture containing 3–4 volumes of acetone to one volume of water. The patent states that all the oligomers are extracted but no mention is made with respect to the monomers.

The process of French 2,092,743 also involves the use of an aqueous ketone. Also, this patent alleges complete extraction of the oligomers but no mention is made of the monomers.

Although a number of processes for the extraction of flavanolic oligomers or similar substances present in vegetable material have already been described (see, for instance, FR Patents 968,589, 1,036,922 and 1,427,100 and GB Patent 1,541,469), it has not been simple to obtain on an industrial scale and in economically acceptable yields extracts almost completely free from monomers, with no remarkable losses or alterations in the dimers and the other oligomers, whose physico-chemical characteristics are clearly similar.

SUMMARY OF THE INVENTION

An object of the present invention is to provide procyanidol oligomer fractions containing less than 1.5% of the undesirable flavanolic monomers.

Still another object is to provide procyanidolic oligomer fractions essentially free from the higher polymers and free from side effects.

Another object of the present invention is to provide procyanidol oligomer fractions with a polymerization degree between 2 and 7.

Still another object of the present invention is to provide a process for the preparation of procyanidol oligomer fractions with a degree of polymerization between 2 and 7.

Still another object is to obtain an extract from *Vitis vinifera* grapeseeds which contains between 24 and 26% of the dimeric proanthocyanidines B1, B2, B3 and B4, about 15% of the trimeric and tetrameric procyanidol oligomers, the balance consisting of a mixture of oligomeric proanthocyanidines having mean molecular weight of about 2000 corresponding to an oligomer having 7 cathechin units.

According to the present invention a crude extract is first obtained according to known methods.

Generally speaking, the processes of the invention are characterized by the following steps:

A) Extraction of the vegetable material with mixtures of water with acetone, methanol or other alcohols, until exhaustion of the catechin derivatives; 80% aqueous acetone is used as the solvent of choice.

B) Concentration of the solvent by evaporation under vacuum to a weight approximately 50% of the weight of the starting vegetable material.

C) Filtration of the concentrate from step B), optionally after standing in refrigerator for 24 hours, to remove any fatty and tannic polymeric residues.

D) Ultrafiltration of the concentrate from step C), under a nitrogen atmosphere, through a tubular plane or capillary membrane of cut-off 100,000 to 1,000.

E) Ultrafiltration of the permeate from step D), from which the high molecular weight substances have been removed, through coiled-spiral membranes of cut-off 3.000 to 600.

F) Optional further fractionation of permeate from step E) by ultrafiltration, limiting the cut-off of the membranes, according to procedures described hereinbelow or subjecting the permeate to fractionation with selective organic solvents.

The permeate from step D) above, before the final purifications, no matter how they are carried out, still contains monomeric substances: in the case of *Vitis vinifera* (+)-catechin and (−)-epicatechin and, in lower amounts, undesired polymeric substances. In order to obtain a good demonomerization degree, the more convenient process comprises a further ultrafiltration on coiled-spiral membranes of cut-off 600 to 3,000 and counter-extraction of the concentrate with ethyl acetate.

The final demonomerized and detannized product is obtained by evaporating the organic phase to a small volume and insolubilizing the concentrate in chloroform or other chlorinated solvents, such as methylene chloride, dichloroethane, etc., Alternatively, the aqueous solution from step C), can be directly extracted with ethyl acetate, and the residue obtained by evaporation of the organic phase, after addition of water, may be subjected to the membrane processes of steps D) and/or E). The aqueous solution from step C), partially concentrated (from 10 to 50% of the weight of the starting plant material), can be extracted with solvent mixtures consisting of ethyl acetate/toluene or other aromatic hydrocarbons, in ratios of 5 to 9 parts of the first solvent and 5 to 1 parts of the second one; extraction is continued with these mixtures until exhaustion in monomeric substances.

The organic phase is counter-extracted with water to recover the amount of dimeric compounds which could accidentally have been extracted by co-solubilization; the combined aqueous phases are extracted with pure ethyl acetate, the organic phase is evaporated under vacuum to small volume and the concentrate is precipitated in a chlorinated solvent.

Alternatively, the mixtures of ethyl acetate with hydrocarbons can advantageously be replaced by other esters, such as isopropyl acetate, amyl acetate, etc. or by methyl-tert-butyl ether. Esters, as well as ether, selectively remove undesired monomeric constituents, besides any lipophilic materials which are usually present in vegetable extracts; the subsequent extraction with ethyl acetate is selective for the oligomeric substances against the polymeric ones, whereby, according to one of the above processes, a product almost free from monomers, which can be allergenic, free as well from polymers having a tanning action, which are irritant to mucosae, can be obtained.

By taking advantage of the selectivity of the above cited solvents and mixtures thereof, extracts having the same chemical composition can be prepared carrying out the fractionation by means of a solid matrix, which selectively absorbs the phenol derivatives, which can be re-eluted from the matrices according to their polymerization degree.

A polystyrene resin, such as the absorption Amberlites® or preferably a Duolite® S-761 can be used as the solid matrix. According to this procedure, the solution from step C) is passed through a column of the selected resin, using about 0,5 liter of support for each 10 g of total solids of the solution. After the absorption of the starting solution, the resin is thoroughly washed with water to completely remove salts,.sugars, organic acids and heavy polymeric fractions, which are excluded due to their steric hindrance. Washing of the resin is continued with a mixture of ethyl acetate and aliphatic or aromatic hydrocarbons, preferably in a 7:3 ratio, until the monomeric substances are completely removed. The extract of the invention is obtained by subsequent elution with aqueous methanol or aqueous acetone, and the resulting eluate is partially evaporated to eliminate the organic solvent. The aqueous concentrate is extracted according to the above reported procedures with ethyl acetate and the residue obtained on concentration, is precipitated by means of chlorinated solvents.

The purified extracts obtained according to the above described processes show, in comparison with those of the prior art, an excellent tolerability and a very good activity with respect to the pathological conditions connected to the cardiovascular system and to superficial and blood circulation. This extract is suited for incorporation in all the usual liquid and solid pharmaceutical formulations.

The extracts according to the present invention, resulting from a suitably selected treatment of the extracts prepared according to the prior art, contain less than 1,5% by weight of monomers and show a higher pharmacological activity than that of the starting extracts, as they are enriched in the procyanidol oligomeric fraction.

It should be noted that the monomers are separated either by ultrafiltration of an aqueous solution of the extract on membranes of cut-off 600 to 3,000, or by selective extraction of the above extract with methyl-tert-butyl ether or with an ester (isopropyl acetate, amyl acetate) or with a mixture of ethyl acetate and aromatic hydrocarbons, such as benzene or toluene. The following non-limiting examples illustrate the invention in details.

BRIEF DESCRIPTION OF THE DRAWINGS

FIG. 3a is the chromatographic report of the chromatogram C;

FIG. 4a is the chromatographic report of chromatogram D;

EXAMPLE 1

Preparation of the demonomerized extract starting from *Vitis vinifera* dry grapeseeds.

100 kg of *Vitis vinifera* grapeseeds are soaked in 150 l of acetone containing 20% water, at room temperature. The extraction solvent is filtered and the extraction is repeated for 4 times more or until exhaustion in phenol derivatives, checking with $FeCl_3$ an aliquot of the extract until the total solids contain less than 0.05% of phenol derivative. The aqueous acetone solutions are combined, acetone is evaporated off by distillation under vacuum until the organic solvent is completely removed. At the end of the concentration, an abundant precipitate forms which, after standing in refrigerator at 4° C. for 24 hours, is centrifuged to give a solid material which comprises lipophilic products and a highly polymerized tannic material. The aqueous solution (about 40 l) is adjusted to pH 6 with 40% NaOH, under nitrogen, and ultrafiltered on a tubular membrane of cut-off 100,000 Enichem (UF-100F), at a temperature below 20° C., and dialyzed with 57 l of water. The permeate, from which polymers have been removed, is acidified with 25% $H_2SO_4$ to pH 3.5 and concentrated by reverse osmosis with coiled-spiral membrane Desal B241-111 until a 30% total solids is obtained. The aqueous concentrate is extracted continuously with an ethyl acetate toluene 8:2 (v/v) mixture by means of a liquid/liquid centrifuge separator until exhaustion of monomeric substances. The exhausted solution is extracted continuously with ethyl acetate until exhaustion of oligomers. The organic phase is concentrated under vacuum to 1.5 liter and diluted with 4.5 l of methylene chloride. The precipitate is centrifuged and dried for 24 hours at 50° C. under vacuum: yield 0.42 kg. This purified extract contains the monomeric substances in a $\leq 1\%$ amount.

EXAMPLE 2

100 kg of *Vitis vinifera* grapeseeds are extracted according to the procedure of Example 1. The permeate, after ultrafiltration on a tubular membrane with cut-off 100,000 (Enichem UF-100F) is acidified to pH 3.5 and ultrafiltered on a coiled-spiral membrane Desal U20-G20 and the solution is dialyzed with 20 volumes of water with respect to the starting solution volume. The concentrate from which the monomeric substances have been removed is further concentrated to a 30% total solids. The aqueous concentrate is extracted with ethyl acetate until exhaustion of the oligomers; the organic phase, after concentration to 1.5 l, is poured into 4.5 l of methylene chloride. The precipitated oligomers are filtered and dried at 50° C. for 24 hours, to obtain 0.45 kg of the same final product as in Example 1.

EXAMPLE 3

100 kg di *Vitis vinifera* grapeseeds are extracted according to the procedure of Example 1. The aqueous solution, after centrifugation of the undesired polymeric substances, is continuously extracted with ethyl acetate in liquid/liquid centrifuge separator, until exhaustion of the phenol substances which can be extracted. The organic phase is concentrated, demineralized water is added to remove the solvent, reaching a final volume of 150 l.

The aqueous solution at pH 3.5 can be subjected either to the treatment reported in Example 1, using tubular membranes of cut-off 100,000 and reverse osmosis, or to a treatment according to the procedure of Example 2, with a membrane of cut-off 100,000 and a coiled-spiral membrane Desal U20-G20. The concentrated aqueous solutions are treated according to the procedures of Examples 1 and 2.

EXAMPLE 4

100 kg of *Vitis vinifera* grapeseeds are extracted according to the procedure of Example 1. The aqueous solution, after filtering off the undesired polymeric fraction, is continuously extracted with ethyl acetate until exhaustion of the polyphenols which can be extracted with this solvent. The organic phase is concentrated to a pasty consistency and the residue is dissolved in 20 l of water, the residual solvent being removed under vacuum. The aqueous solution is absorbed on a column containing 30 l of the polystyrene resin Duolite S-761, continuing the water elution until obtaining nearly discolored water. Then elution is continued with an ethyl acetate/toluene 7:3 mixture till complete removal of the monomeric substances, checking the elimination by thin layer chromatography, using a butyl acetate/acetic acid/formic acid/water 8:1:1:1 mixture as the eluent and chlorosulfonic acid in acetic acid as the developer. The oligomeric fraction is obtained by continuing the elution with pure ethyl acetate. The organic solution containing mainly dimeric, trimeric and tetrameric substances is concentrated to 1 liter and poured into 3 l of methylene chloride. After filtration and drying, 210 g of a product containing monomers in an amount less than 0.1% are obtained.

Alternatively, the column is eluted with methanol instead of pure ethyl acetate; the alcoholic phase is concentrated to a small volume and the residue is diluted with 30 l of water; the aqueous phase is counter-extracted with ethyl acetate, following the procedure of Examples 1 and 2 to obtain the product. In this instance, 405 g of the product are obtained, which is nearly the same as the above described ones.

EXAMPLE 5

100 kg of *Vitis vinifera* grapeseeds are extracted according to the procedure of Example 1. After centrifugation of the polymeric substances, the aqueous solution having about 8% total solids is diluted to reach about 5% total solids and chromatographed on a column containing 50 l of Duolite S-761, thoroughly washing with about 500 l of water, so as to completely remove salts and sugars which are abundantly present in the extract. Then, purification of the oligomers is carried out as in Example 4, washing the column first with ethyl acetate/toluene, then with methanol. After precipitation from methylene chloride, 423 g of an oligomeric fraction, similar to that from the other Examples, are obtained.

EXAMPLE 6

100 kg of *Vitis vinifera* grapeseeds are extracted according to the procedure of Example 1. The aqueous solution after filtering off the polymeric material is extracted with 10 × 50 l portions of an ethyl acetate/toluene 8:2 mixture. The organic phase, containing fatty materials and the monomers, is counter-washed with 20 l of water. The combined aqueous phases are extracted with 10 × 50 l of ethyl acetate saturated with water; the organic phase is concentrated to a pasty consistency and the residue is taken up into 7 l of water, the residual solvent being evaporated under vacuum. The slightly turbid aqueous solution is treated with 750 g of NaCl. A precipitate is formed which, after the solution stands in refrigerator for 24 hours, is filtered. The filtrate is extracted with 10 × 7 l of ethyl acetate; the organic solution is concentrated to 1 liter and the concentrate is poured into 3 l of methylene chloride. After filtration and drying according to the procedures described in the above Examples, 402 g of a final product are obtained, which is similar to the same product described in the preceding examples.

EXAMPLE 7

100 kg of *Vitis vinifera* grapeseeds are extracted according to the procedure of Example 2. The permeate from the coiled-spiral membrane Desal U20-G20 of Example 2 and/or the aqueous solution obtained from the ethyl acetate/toluene 8:2 mixture according to the procedure of Example 1, after concentration to a pasty residue and substitution of the solvent with water, are ultrafiltered on a coiled-spiral membrane U20-G5. The concentrated aqueous solution, after dialysis, is nearly free of monomers and contains the oligomers which are extracted with ethyl acetate. The organic solution is concentrated to 0.1 liter and precipitated with 0.5 l of methylene chloride.

38.1 g of a product containing 38% dimeric substances and about 1% monomeric catechins are obtained.

Comparison between the product according to the present invention and the product prepared according to French 2,092,763 and U.S. Pat. No. 4,963,527.

The product according to Examples 4 and 5 was compared with the product prepared according to French 2,092,743 and U.S. Pat. No. 4,963,527. The two products were analyzed by Gel Permeation Chromatography (GPC) and HPLC in order to determine the amount of monomers, particularly gallic acid, catechin and epicathechin.

From the comparison of the above chromatograms, it can be seen that the monomers catechin and epicatechin in the extracts obtained according to the present invention are strongly reduced with respect to the extract obtained according to FR 2092743.

Figure 5:
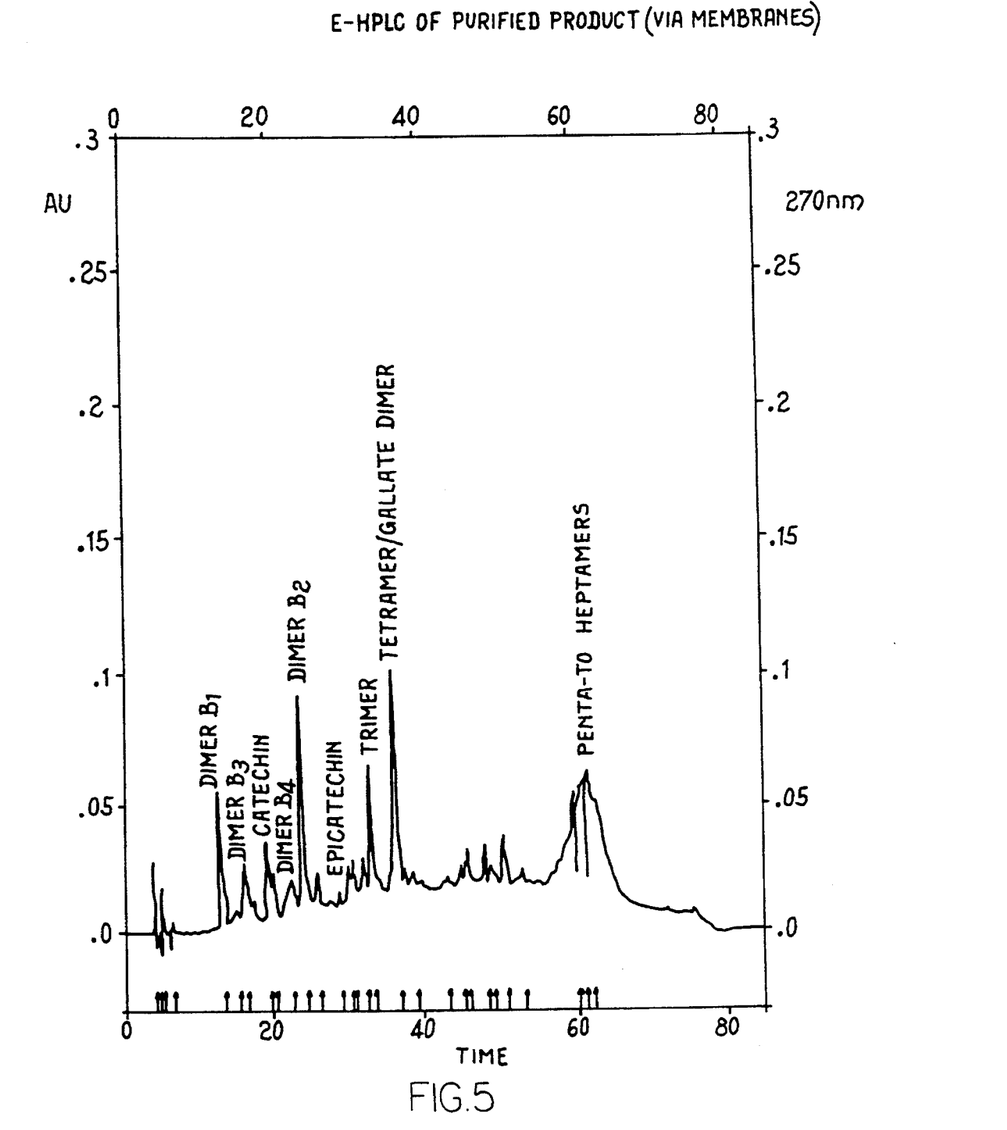
FIG. 5 is the HPLC chromatogram E of the product purified according to Examples 1–3.
Figure 5A:
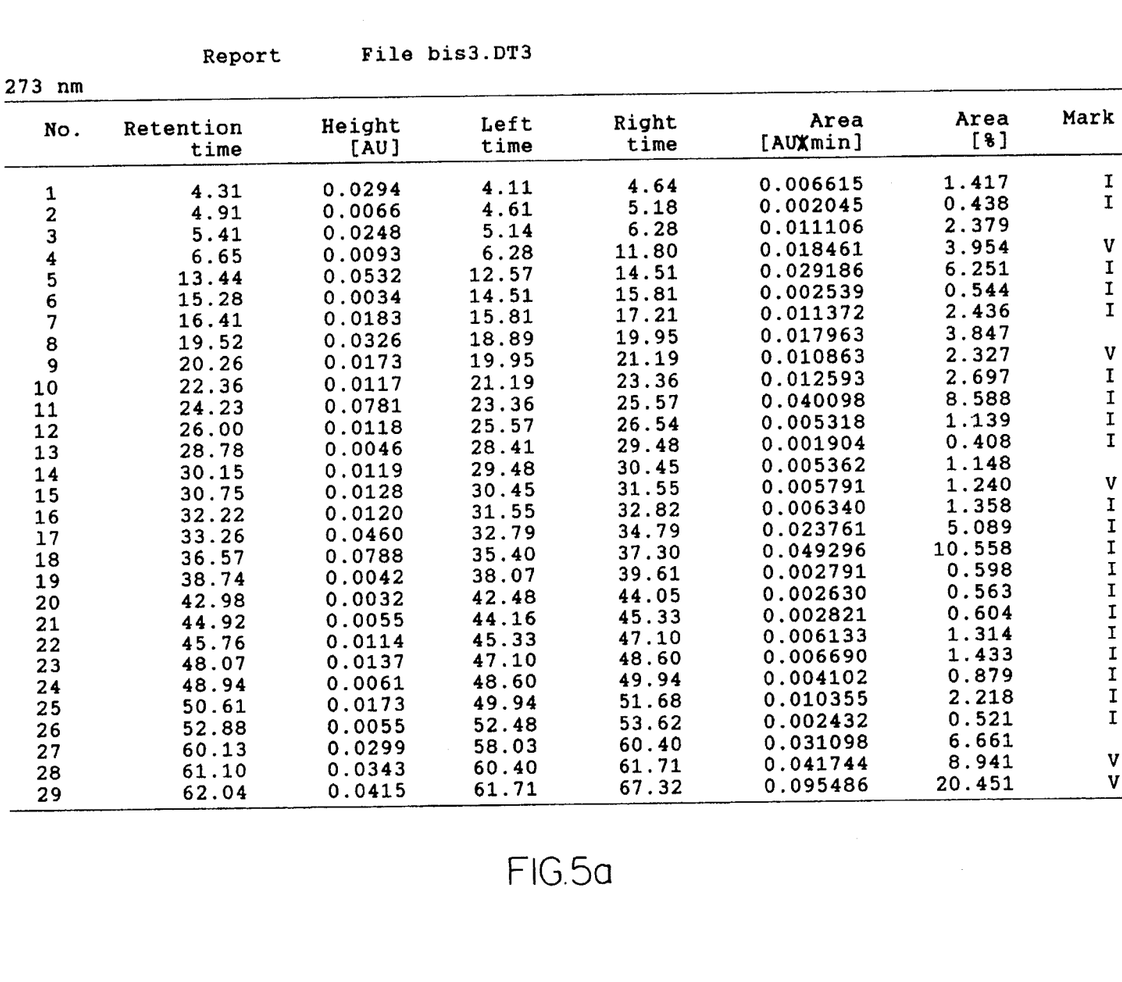
FIG. 5a is the chromatographic report of chromatogram E.

Chromatogram E shows that the purification with membrane ultrafiltration leads to better results than the ones obtained by purification with solvents.

Figure 1:
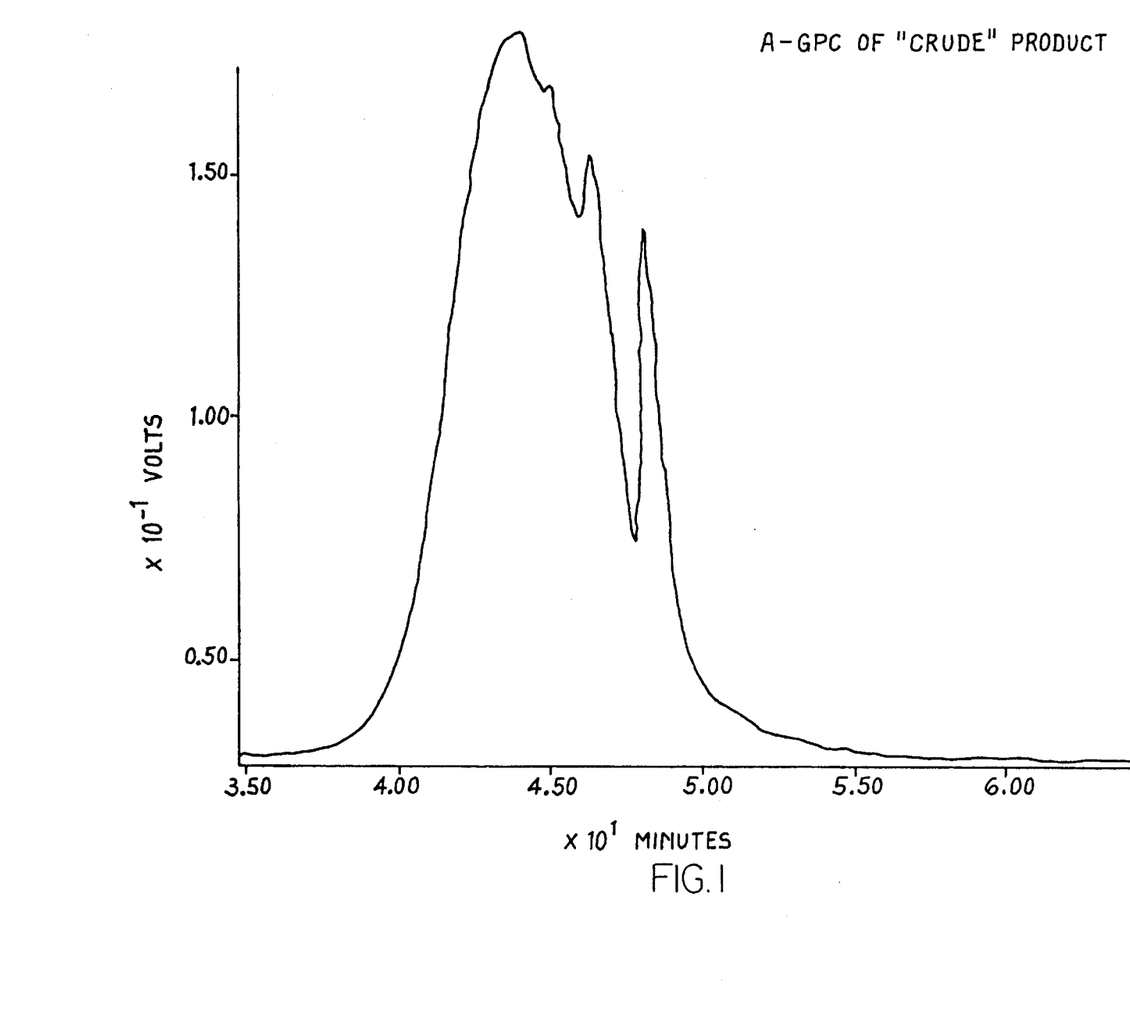
FIG. 1 shows the gel permeation chromatogram A (GPC) of the crude product.
Figure 2:
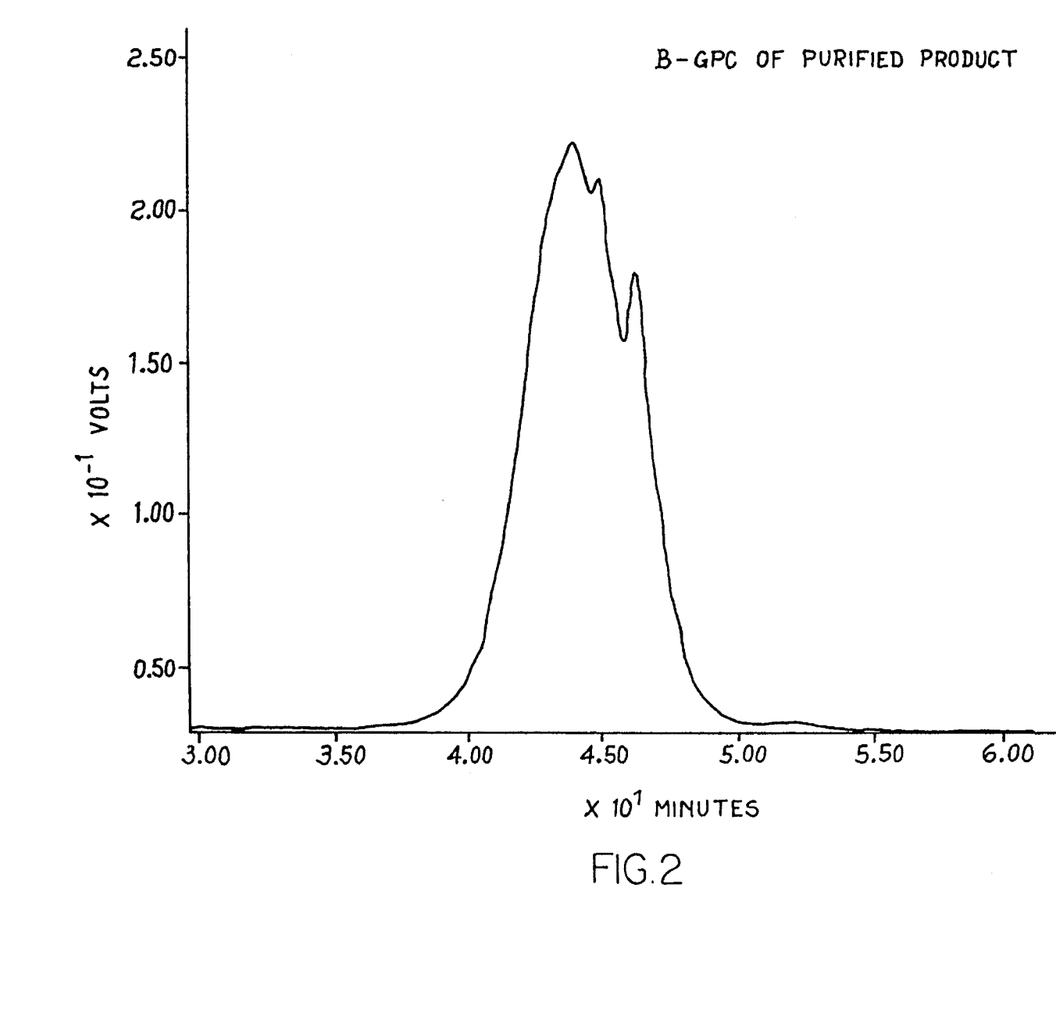
FIG. 2 shows the gel permeation chromatogram B of the purified product.
Figure 3:
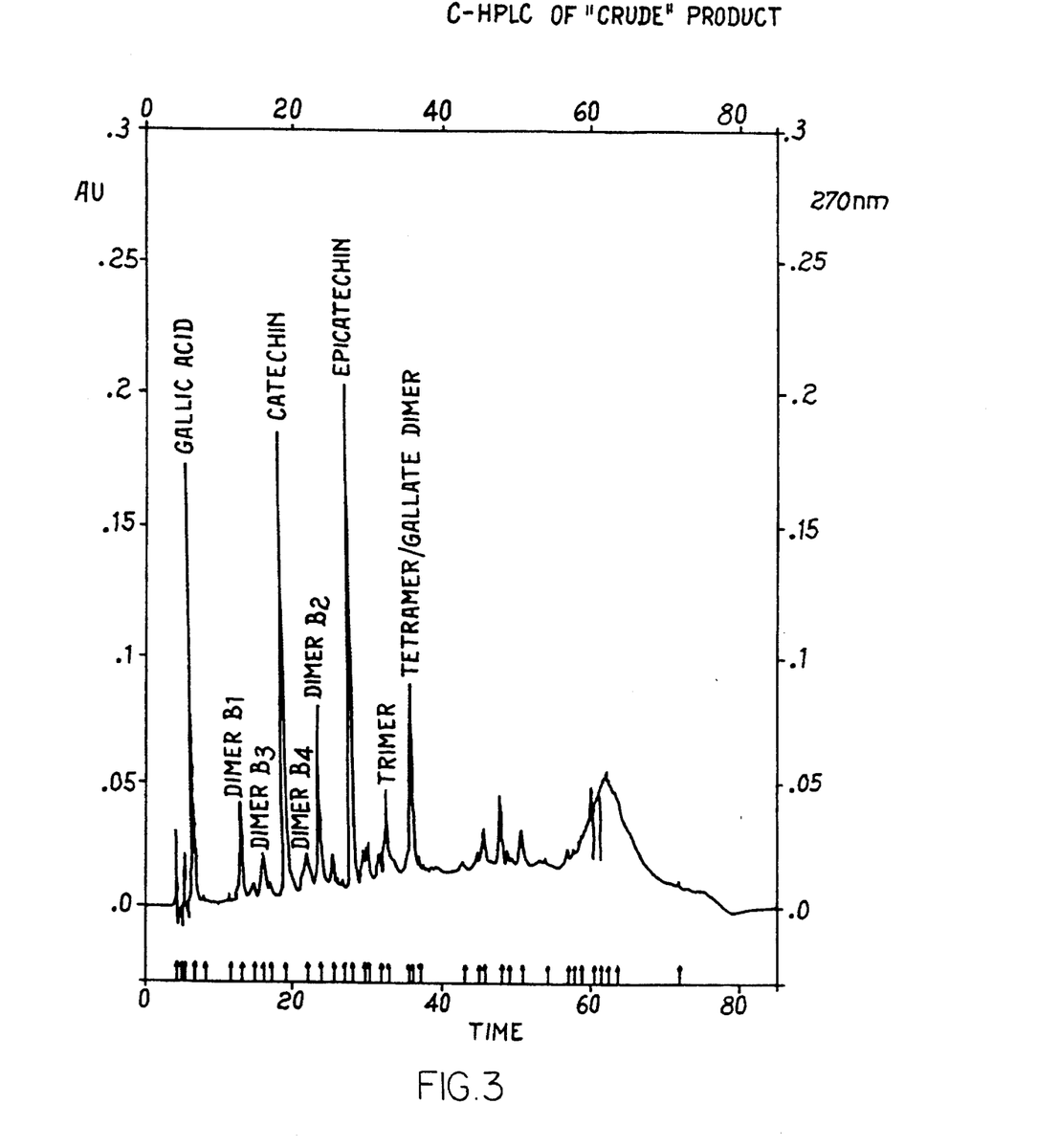
FIG. 3 shows the HPLC chromatogram C of the crude product.
Figure 4:
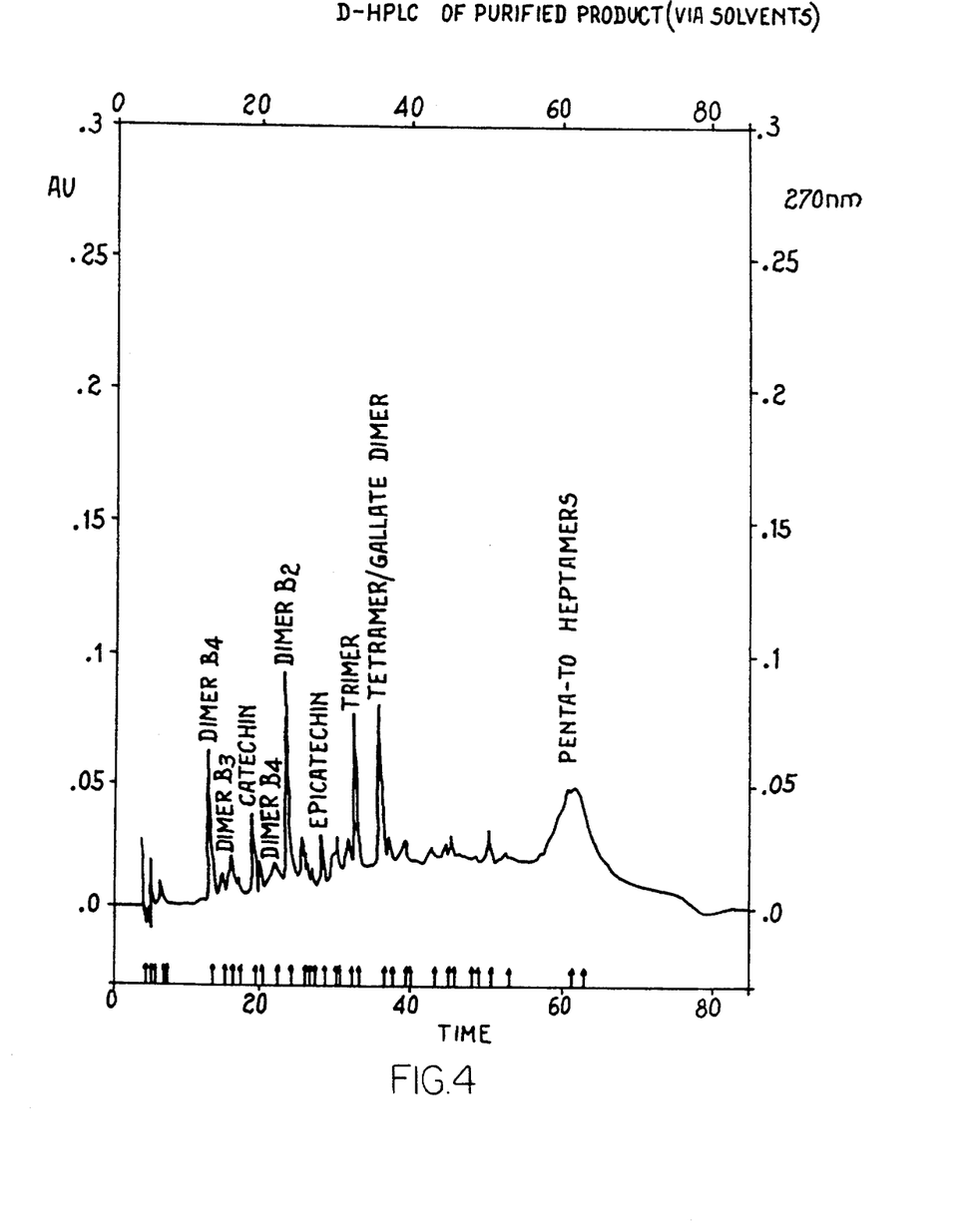
FIG. 4 shows the HPLC chromatogram D of the purified product, as described in Examples 4 and 5.

The chromatographs show the peaks corresponding to each constituent. Specifically, the chromatograms show a very high amount of the monomers in the extracts of the reference and very low amount in chromatograms B, D and E. Further chromatogram E, of the product prepared as described in Examples 1–3, shows that the product prepared in Examples 1–3 where ultrafiltration is used, is superior to the product prepared in Examples 4 and 5 in which solvent extraction is used.

What is claimed is:

1. A process for the preparation of an extract enriched in procyanidol oligomers from *Vitis vinifera* grapeseeds, said extract containing less than 1.5% by weight of flavanolic monomers, less than 1% by weight of (+)-catechin and between 2 and 7 procyanidol units which comprises the steps of:

a) extracting said *Vitis vinifera* grapeseeds with an aqueous acetone or aqueous methanol solution until exhaustion of catechin derivatives to obtain an aqueous acetone or aqueous methanol solution;

b) concentrating said aqueous acetone or aqueous methanol solution from step a) under vacuum to remove the acetone or methanol to obtain a precipitate containing fatty and tannic polymeric residues and a first aqueous solution;

c) filtering said precipitate from the first aqueous solution from step b) to remove said precipitate containing the fatty and tannic polymeric residues from said first aqueous solution;

d) subjecting said first aqueous solution from step c) to ultrafiltration on membranes of cut-off 100,000 to give a first permeate;

e) subjecting said first permeate from step d) to ultrafiltration to remove most of the flavanolic monomers on membranes of cut-off 3,000 to 600 to obtain a second permeate;

f) exhaustively extracting said second permeate from step e) with ethyl acetate to obtain an ethyl acetate solution containing said procyanidol oligomers;

g) concentrating and precipitating said oligomers from the ethyl acetate solution of step f) with a chlorinated hydrocarbon selected from the group consisting of chloroform, methylene chloride, and dichloroethane; and h) recovering said extract enriched in procyanidol oligomers.

2. The process according to claim 1 wherein said first aqueous solution from step b) is adjusted to a pH of 6.

3. The process according to claim 1 wherein in step a) said *Vitis vinifera* grapeseeds are extracted with 80% aqueous acetone or aqueous methanol solution and in step b) said aqueous acetone or aqueous methanol solution is concentrated to about 50% of the weight of said *Vitis vinifera* grapeseeds.

4. The process as claimed in claim 1 wherein tubular, capillary, coiled-spiral or plane membranes are used for the ultrafiltration.

5. A process for the preparation of an extract enriched in procyanidol oligomers from *Vitis vinifera* grapeseeds, said extract containing less than 1.5% by weight of flavanolic monomers, less than 1% by weight of (+)-catechin and between 2 and 7 procyanidol units which comprises the steps of:

a) extracting said *Vitis vinifera* grapeseeds with an aqueous acetone or aqueous methanol solution until exhaustion of catechin derivatives to obtain an aqueous acetone or aqueous methanol solution;

b) concentrating said aqueous acetone or aqueous methanol solution from step a) under vacuum to remove the acetone or methanol to obtain a precipitate containing fatty and tannic polymeric residues and a first aqueous solution;

c) filtering said precipitate from the first aqueous solution from step b) to remove said precipitate containing the fatty and tannic polymeric residues from said first aqueous solution;

d) subjecting said first aqueous solution from step c) to ultrafiltration on a membrane of cut-off 100,000, to give a first permeate;

e) exhaustively extracting said first permeate from step d) with a water-immiscible organic phase consisting of an 8:2 mixture of ethyl acetate and toluene or with an ester selected from the group consisting of isopropyl acetate, amyl acetate or with methyl-tert-butyl-ether to remove most of the flavanolic monomers from said organic phase;

f) counterextracting said organic phase from step e) with water to obtain a second aqueous solution;

g) extracting said oligomers in said second aqueous solution with ethyl acetate to obtain an ethyl acetate extract;

h) concentrating the ethyl acetate extract under vacuum and adding chloroform, methylene chloride or dichloromethane to obtain a precipitate of procyanidol oligomers; and i) recovering said extract enriched in procyanidol oligomers.

6. A process for the preparation of an extract enriched in procyanidol oligomers from *Vitis vinifera* grapeseeds, said extract containing less than 1.5% by weight of flavanolic monomers, less than 1% by weight of (+)-catechin and between 2 and 7 procyanidol units which comprises the steps of:

a) extracting said *Vitis vinifera* grapeseeds with an aqueous acetone or aqueous methanol solution until exhaustion of catechin derivatives, to obtain an aqueous acetone or aqueous methanol solution;

b) concentrating said aqueous acetone or aqueous methanol solution from step a) under vacuum to remove the acetone or methanol to obtain a precipitate containing fatty and tannic polymeric residues and a first aqueous solution;

c) filtering said precipitate from the first aqueous solution from step b) to remove the precipitate containing the fatty and tannic polymeric residues from the said first aqueous solution;

d) exhaustively extracting said first aqueous solution from step c) with ethyl acetate to obtain an ethyl acetate solution;

e) concentrating said ethyl acetate solution from step d) to a pasty residue and dissolving said pasty residue in water to obtain a second aqueous solution;

f) passing said second aqueous solution from step e) through a chromatographic column filled with a polystyrene resin;

g) eluting said column with a mixture of ethyl acetate and toluene to remove the flavanolic monomers;

h) eluting said column with ethyl acetate to obtain an ethyl acetate solution of said procyanidol oligomers;

i) concentrating said ethyl acetate solution to obtain an extract of said oligomers;

j) precipitating said extract of said oligomers with methylene chloride; and k) recovering said extract enriched in procyanidol oligomers.

7. An extract from *Vitis vinifera* grapeseeds enriched in procyanidol oligomers, said extract containing less than 1.5% by weight of flavanolic monomers, less than 1% by weight of (+)-catechin, and between 2 and 7 procyanidol units.

8. The extract according to claim 7 which contains between 24 and 26% of by weight dimeric proanthocyanidines B1, B2, B3 and B4 and about 15% by weight of trimeric and tetrameric procyanidol oligomers, the balance consisting of a mixture of procyanidol oligomers having a mean molecular weight up to 2000 and corresponding to an oligomer having 7 catechin units.

* * * * *